United States Patent
Davies et al.

(10) Patent No.: US 9,636,249 B2
(45) Date of Patent: May 2, 2017

(54) SEAL FOR CONTROLLED EVACUATION OSTOMY APPLIANCE

(75) Inventors: Geraint Davies, Cambridge (GB); John Cline, New Brunswick, NJ (US); Christopher C. Gregory, Newtown, PA (US); Alan Cucknell, Cambridge (GB); Julian Scarfe, Cambridge (GB); Pete Cauwood, Cambridge (GB)

(73) Assignee: CONVATEC TECHNOLOGIES INC., Reno, NV (US)

( * ) Notice: Subject to any disclaimer, the term of this patent is extended or adjusted under 35 U.S.C. 154(b) by 0 days.

(21) Appl. No.: 11/200,747

(22) Filed: Aug. 10, 2005

(65) Prior Publication Data

US 2006/0058577 A1 Mar. 16, 2006

Related U.S. Application Data

(60) Provisional application No. 60/610,357, filed on Sep. 16, 2004.

(51) Int. Cl.
  *A61F 2/02* (2006.01)
  *A61F 5/44* (2006.01)
  *A61F 5/441* (2006.01)
  *A61F 5/445* (2006.01)

(52) U.S. Cl.
  CPC ............ *A61F 5/441* (2013.01); *A61F 5/445* (2013.01)

(58) Field of Classification Search
  USPC ....... 604/332–345, 355; 600/30–32; 128/887
  See application file for complete search history.

(56) References Cited

U.S. PATENT DOCUMENTS

| | | | |
|---|---|---|---|
| 2,931,353 A | | 4/1960 | Kitzul |
| 4,121,589 A | * | 10/1978 | McDonnell ................. 604/337 |
| 4,231,369 A | * | 11/1980 | Sorensen et al. ............ 604/336 |
| 4,258,704 A | * | 3/1981 | Hill ............................... 600/32 |
| 4,950,223 A | | 8/1990 | Silvanov |
| 4,979,947 A | | 12/1990 | Berman et al. |
| 4,981,465 A | * | 1/1991 | Ballan et al. .................. 600/32 |
| 5,188,623 A | | 2/1993 | Kok et al. |
| 6,673,982 B1 | * | 1/2004 | Chen et al. ................... 604/378 |
| 6,723,079 B2 | * | 4/2004 | Cline ............................ 604/337 |
| 8,070,737 B2 | * | 12/2011 | Cline .................... A61F 5/445 128/887 |
| 8,217,221 B2 | * | 7/2012 | Davies ................... A61F 5/445 604/322 |

(Continued)

FOREIGN PATENT DOCUMENTS

| | | |
|---|---|---|
| EP | 1 348 412 | 1/2003 |
| EP | 1 346 711 | 9/2003 |

(Continued)

*Primary Examiner* — Michele M Kidwell
(74) *Attorney, Agent, or Firm* — Wilson Sonsini Goodrich & Rosati (57) ABSTRACT

A stoma seal is described for a controlled evacuation ostomy appliance. The stoma seal may have a liquid-responsive property, such as hydrophobic, hydrophilic or absorptive. The stoma seal may have a non-smooth surface, e.g., at a microstructure scale. The non-smooth surface may consist of tortuous channels, protruding seals, or a confronting apertured or porous layer. The liquid-responsive property and/or the non-smooth surface may facilitate separation of flatus from faecal matter and/or facilitate venting of flatus while obstructing stool.

11 Claims, 7 Drawing Sheets

(56) References Cited

U.S. PATENT DOCUMENTS

2003/0040727 A1 2/2003 Boulanger et al.

FOREIGN PATENT DOCUMENTS

| EP | 1346711 A | | 9/2003 | | |
|----|-----------|---|--------|---|---|
| EP | 1 348 412 A1 | * | 10/2003 | ............. | A61F 5/445 |
| EP | 1348411 | | 10/2003 | | |
| GB | 1 571 382 | * | 7/1980 | ............... | A61F 5/44 |
| WO | WO 9844880 A1 | * | 10/1998 | ............. | A61F 5/441 |

* cited by examiner

SEAL FOR CONTROLLED EVACUATION OSTOMY APPLIANCE

This application is based on Provisional Application Ser. No. 60/610,357, filed Sep. 16, 2004, and priority on that application is hereby claimed.

FIELD OF THE INVENTION

The present invention may relate to the field of ostomy appliances, and in particular to such appliances which can be used to control stomal discharge (so called controlled evacuation appliances). One aspect of the invention may relate to a seal for such an appliance for blocking the discharge of stool from the stoma.

BACKGROUND OF THE INVENTION

The creation of an ostomy (stoma) is the therapy for many sufferers of diseases or injury of the gastrointestinal or urinary tract. An ostomy is the rerouting of the tract through the abdominal wall to outside the patient's body. Once a stoma has been created, the patient must, usually for the rest of his or her life, use a device worn on the body for capturing or containing the body waste. This has traditionally been done with a bag or pouch attached to the body with adhesive patches or constricting belts. However, the wearing of such a pouch can be an extremely embarrassing and belittling experience for many ostomates. A pouch requires significant changes in a person's public and personal activities.

A controlled evacuation appliance offers the potential for an ostomate to return to some form of normality. The appliance is used to block the stoma mouth, in order to store the liquid and/or solid stool temporarily inside the tract. The appliance is deactivatable and/or removable manually when the ostomate desires to discharge the stool from the stoma. A design feature which distinguishes a controlled evacuation appliance from a conventional ostomy pouch is the presence of a stoma seal, for blocking the stoma mouth.

U.S. Pat. No. 4,950,223 describes a controlled evacuation appliance in the form of an inflatable ostomy plug. The plug includes a stoma seal in the form of an inflatable bung which fits inside the stoma. In use, the ostomate can inflate the bung to plug the stoma, by compressing a bellows pump located externally on the plug. The bung is deflated by an opposite movement of the bellows. Although this example of an inflatable plug is highly appealing in theory, it suffers from certain impracticalities. In particular, it is not possible to vent flatus while the bung is inflated in the stoma. Flatus can only be vented when the bung is collapsed to allow discharge of body waste from the stoma. This presents severe limitations for the ostomate, because the ostomate will have to collapse the bung very frequently in order to avoid an uncomfortable accumulation of flatus within the body.

The venting of flatus for a controlled evacuation device remains a significant problem. It is technically difficult to provide a controlled evacuation appliance that can achieve a reliable seal in use to block escape of stool while allowing flatus to vent through or around the seal.

Flatus vents are known from the field of ostomy pouches. However, in a pouch, there is no equivalent stoma seal that has to withstand prolonged contact with stool. Also, in a pouch, the flatus is able to separate easily from the stool because the stool drops under gravity into the collection region of the pouch. The vent arrangements for pouches are designed to withstand only occasional (accidental) contact with stool, and do not perform reliably if exposed to prolonged contact with stool, especially in direct contact with the stoma.

SUMMARY OF THE INVENTION

Broadly speaking, the invention may provide a stoma seal for a controlled evacuation ostomy appliance. The stoma seal may be configured to provide an obstruction to faecal matter (e.g., one or more of solid, semi-solid or liquid stool), while allowing efficient venting of flatus. The flatus may pass through and/or along and/or around the seal. The seal may be porous to allow flatus to vent through the seal. Alternatively, the seal may be impervious, in which case flatus may be directed along the surface of the seal at the interface between the seal and the faecal matter. The stoma seal may be configured to withstand prolonged contact with stool.

The stoma seal may be configured to facilitate separation of flatus from stool, to enhance the seal performance in terms of obstructing stool while allowing efficient venting of flatus.

The stoma seal may have one or more of the following characteristics:

(a) The stoma seal may be configured to repel and/or attract and/or absorb liquid. Such behaviour towards liquid may greatly increase the gas separation function at the stoma seal surface. The behaviour towards liquid may be provided by one or more of the following:

(a) (i) At least a portion of the stoma seal may be hydrophobic. For example, the stoma seal may carry or comprise hydrophobic material. The stoma seal may have a hydrophobic coating, or the surface of the material may be hydrophobic (e.g. the stoma seal may comprise PTFE, which is hydrophobic).

(a) (ii) At least a portion of the stoma seal may be hydrophilic. For example, the stoma seal may carry or comprise hydrophilic material. The stoma seal may have a hydrophilic coating, or the surface of the material may be hydrophilic.

(a) (iii) At least a portion of the stoma seal may carry or comprise carbon, for example, activated carbon.

(a) (iv) At least a portion of the stoma seal may have a micro-rough surface texture. For example, the stoma seal may carry a micro-rough coating, such as particles embedded in a matrix.

(a) (v) At least a portion of the stoma seal may be liquid absorbent. For example, the stoma seal may carry a liquid absorbent coating. The liquid absorbent may be a super-absorbent, for example, super-absorbent particles embedded in a matrix.

(b) The stoma seal may be configured to have a non-smooth surface structure and/or texture and/or geometry. The non-smoothness may help break up the flow of faecal matter, and/or to trap liquid and solid particles, and/or to encourage flow separation of the gas phase. In addition, by creating surface-induced variations in the cohesive and/or capillary forces in the interface between the surface and the faecal matter in contact with the surface, "break-out" paths may be formed along which flatus "bubbles" may pass (e.g. in preference to liquid) through the meniscus at the interface.

For example, the non-smoothness may be provided by one or more of the following:

(b) (i) Tortuous narrow miniature pathways or channels may be provided in the surface of the stoma seal. The pathways may be defined by ridges and valleys formed in the surface. The pathways may extend generally outwardly and/or away from a region of the surface in contact with the stoma, to guide flatus outwardly and/or away. The pathways may extend generally in the direction in which flatus vents away from the stoma (e.g. parallel to the direction of flow of faecal matter).

(b) (ii) The surface of the stoma seal may be shaped to define a microstructure of projecting ridges and/or ribs. The ridges/ribs may be configured to present a lateral obstruction to the passage of faecal matter. The ridges/ribs may form a series of successive seals, e.g., against the stoma. The ridges/ribs may extend generally perpendicular to the direction in which flatus flows to vent.

(b) (iii) The surface of the stoma seal may be generally contoured, so as to be non-flat. The non-flat configuration may define a contour at the microstructure level, or larger.

(b) (iv) A porous and/or apertured layer may be placed against, or may surround, the stoma seal. For example, the layer may be a mesh or net. The layer may impart a non-smooth surface structure or texture to the stoma seal. The scale of the structure may generally lie in the range of from about 0.01 mm to about 10 mm, and preferably in the range of from about 0.1 mm to about 5 mm.

(c) Any of the above sub-features within aspects (a) and (b) may be combined together, and any of the above aspects (a) and (b) may be combined together.

(d) The features (a), (b) and (c) above may be used on any surface or surface portion of the stoma seal. The features may be applied to an internal or external surface of the stoma seal. The features may be applied to any surface of the stoma seal that may contact faecal matter. For example, the features may be applied to a surface in contact with, or facing, the stoma and/or peristomal tissue. Additionally or alternatively, if the stoma seal is porous or is hollow (e.g. if the stoma seal has internal channels or cavities), then an internal surface of the stoma seal may be provided with any of the above features.

(e) The stoma seal may comprise a plurality of elements which together act as a seal to obstruct the passage of faecal matter while allowing venting of flatus. For example, the elements may comprise a plurality of fibres, filaments or tubes arranged in bundles and/or as a mat. Some or all of the elements may be provided with one of more of the features described hereinbefore.

Further features and advantages of the invention will be apparent from the following detailed description. Although certain significant features have been described above and in the appended claims, the Applicant claims protection for any novel feature or idea described herein and/or illustrated in the drawings, whether or not emphasis has been placed thereon.

BRIEF DESCRIPTION OF THE DRAWINGS

Non-limiting preferred embodiments of the invention are now described, by way of example, with reference to the accompanying claims and drawings, in which:

DETAILED DESCRIPTION OF PREFERRED EMBODIMENTS

Referring to FIGS. 1 to 4, a controlled evacuation ostomy appliance 10 may be illustrated for controlling discharge from a person's stoma 12. The appliance 10 may comprise a stoma seal 14 for blocking or occluding the mouth of the stoma 12, in order to substantially contain faecal matter in the region of the stoma 12. The appliance 10 may further comprise an adhesive wafer 16 for attaching the appliance to the peristomal skin 18, and a housing 20.

Figure 1:
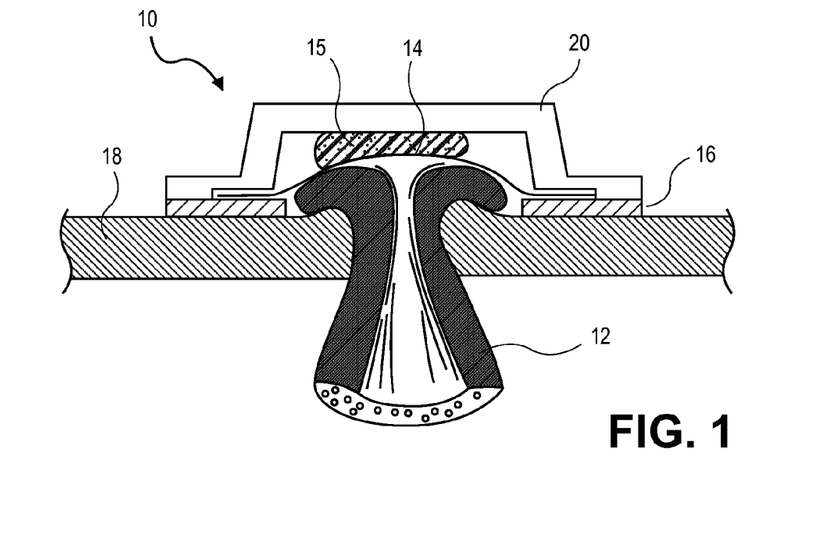
FIG. 1 is a schematic cross section showing a first example stoma seal of a controlled evacuation ostomy appliance.
Figure 1A:
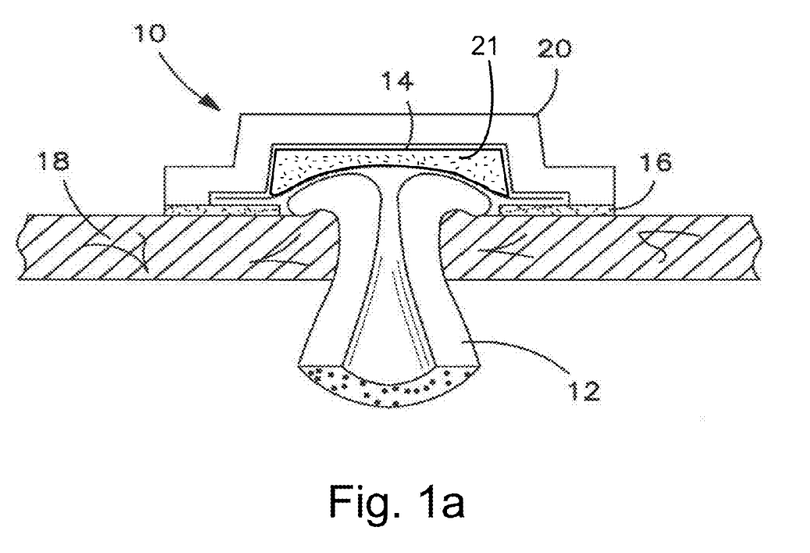
FIG. 1a is a schematic cross sectional view showing a first example stoma seal of a controlled evacuation ostomy appliance with a resiliently compressible foam.
Figure 2:
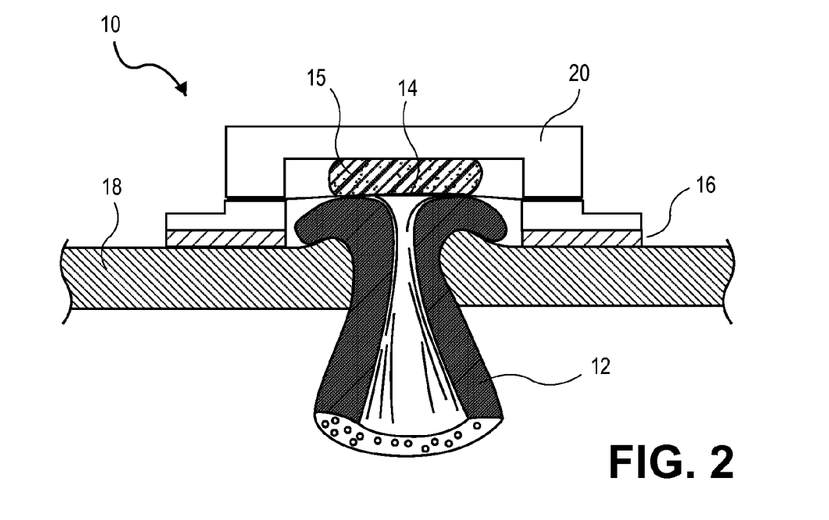
FIG. 2 is a schematic cross section showing a second example stoma seal of a controlled evacuation ostomy appliance.
Figure 2A:
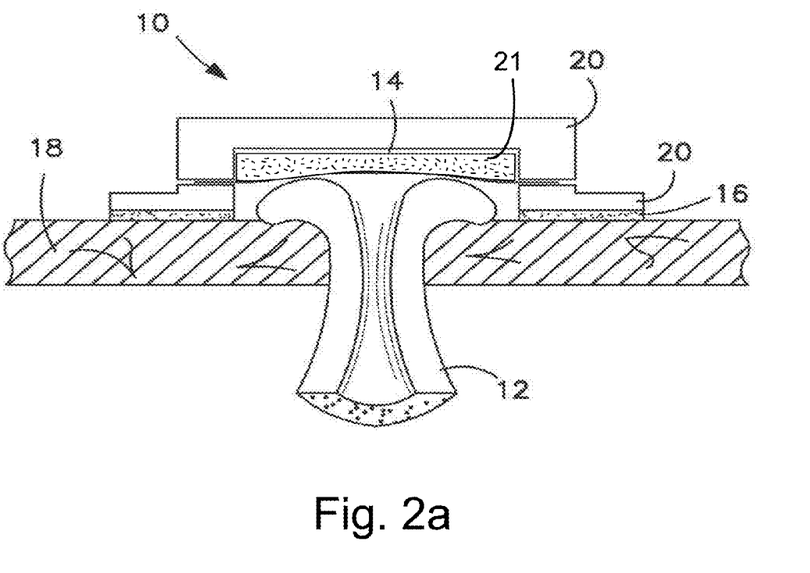
FIG. 2a is a schematic cross sectional view showing a second example stoma seal of a controlled evacuation ostomy appliance with a resiliently compressible foam.
Figure 3:
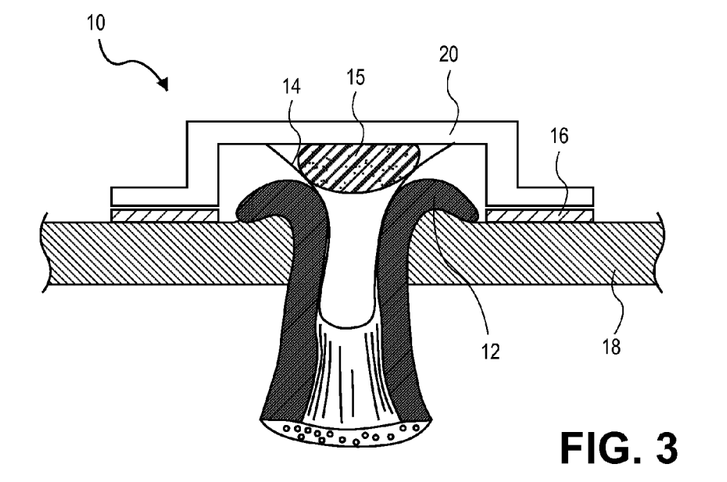
FIG. 3 is a schematic cross section showing a third example stoma seal of a controlled evacuation ostomy appliance.

The stoma seal 14 may take a variety of different forms, and several different examples are illustrated in FIGS. 1 to 4. In FIG. 1, the stoma seal 14 may contact, and form a seal against, the peristomal skin 18 to prevent escape of faecal matter. In FIG. 2, the stoma seal 14 may contact, and form a seal against, the external tissue of the stoma 12, to prevent escape of faecal matter. The configurations of FIGS. 1 and 2 may be referred to as non-entrant, as the stoma seal 14 may not enter the stoma 12. In FIG. 3, the stoma seal 14 may be provided in the form of a plug that may contact, and seal against, an internal surface of the stoma 12. The stoma seal 14 may be provided in the form of a membrane (e.g. surrounding a support) or the stoma seal 14 may have a self-supporting three-dimensional plug shape.

Figure 4:
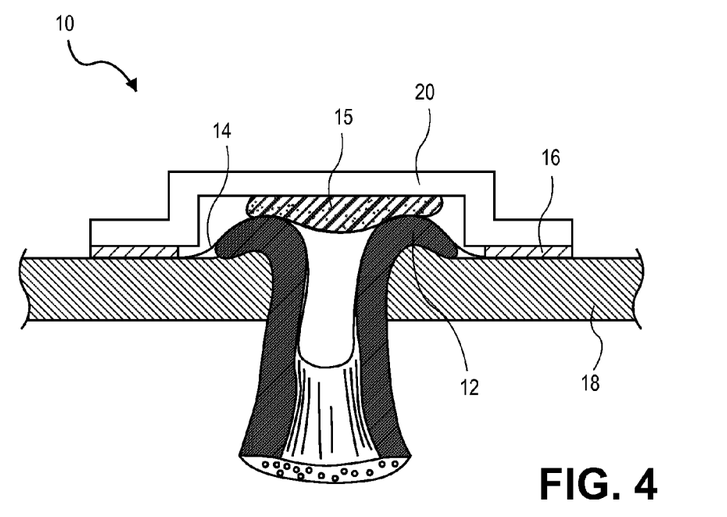
FIG. 4 is a schematic cross section showing a fourth example stoma seal of a controlled evacuation ostomy appliance.

Two or more of the above possibilities may also be combined, as illustrated in FIG. 4, in which the stoma seal 14 may contact, and seal against, an internal surface of the stoma 12, also an external surface of the stoma 12, and also the peristomal skin 18. The configurations of FIGS. 3 and 4 may be referred to as entrant or plugs, because the stoma seal 14 may enter the stoma 12.

The stoma seal 14 may be supported by any suitable support 15 for pressing the stoma seal 14 against the stoma 12/skin 18. For example, the support may be inflatable, or it may be resilient, e.g. compressible foam 15. The stoma seal 14 may be configured to substantially obstruct the passage of faecal matter (e.g. at least one of solid, semi-solid, or liquid stool), while facilitating separation and venting of flatus.

The stoma seal 14 may be porous (or comprise a porous portion) to allow flatus to vent therethrough, while obstructing the passage of faecal matter. In that case, one or more vent ports 22 may be arranged in the housing 20 to communicate with the rear of the stoma seal 14. Alternatively, the stoma seal 14 may be impermeable (or comprise an impermeable portion), in which case flatus may flow along the interface between the stoma seal 14 on the confronting matter (e.g. faecal matter, or the tissue of the stoma 12, or the periostomal skin 18). One or more vent ports 22 may be arranged in the housing to communicate with a lateral periphery of the stoma seal 14.

The stoma seal 14 may be configured to facilitate separation of flatus from the faecal matter (e.g., at least one of solid, semi-solid or liquid stool).

Figure 5:
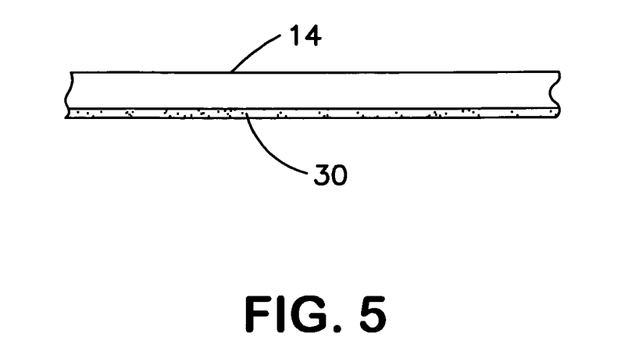
FIG. 5 is a detailed schematic cross section of an example stoma seal having a coating.

Referring to FIG. 5, the stoma seal 14 may comprise (e.g. as a coating 30) a material that may be have one or more of the following properties:

(a) The material may be hydrophobic. For example, the stoma seal 14 may comprise, or carry a coating of, of hydrophobic material, such as PTFE.

(b) The material may be hydrophilic.

(c) The material may be carbon.

Figure 6:
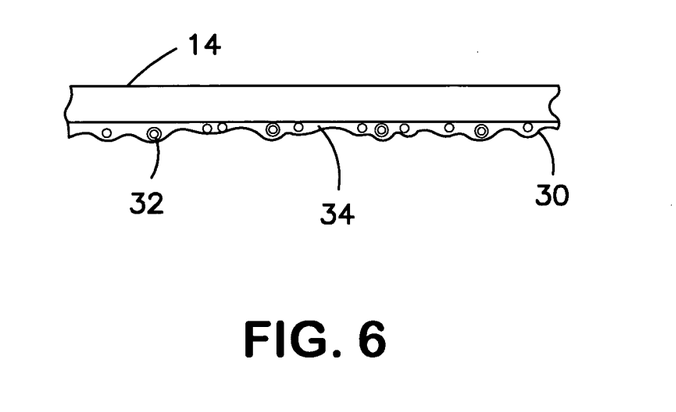
FIG. 6 is a detailed schematic cross section of a further example stoma seal carrying particles.

(d) The material may have a rough surface texture, for example, a micro-rough surface texture. Referring to FIG. 6, the material may be a micro-rough coating 30 of particles 32 embedded in a matrix 34.

(e) The material may be liquid absorbent. For example, material may be a superabsorbent. In a similar manner to FIG. 6, the material may consist of superabsorbent particles embedded in a matrix.

The above features may cause the stoma seal 14 to attract, repel or absorb liquid, or one or more components of liquid stool. Such behaviour towards liquid may increase the gas separation function at the surface of the stoma seal 14. As explained above, increasing the gas separation may facilitate venting of flatus at the stoma seal 14.

Figure 7:
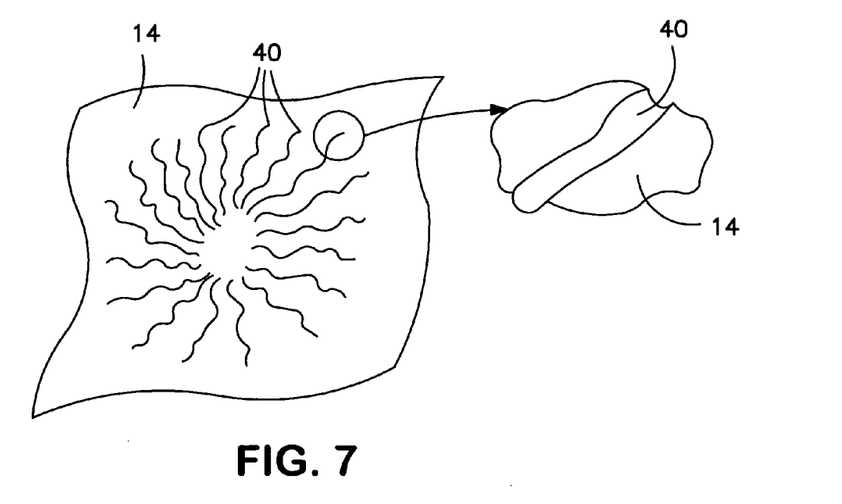
FIG. 7 is a schematic underside perspective view of a further example stoma seal having tortuous channels.

In addition to, or as an alternative to, any of the preceding features, the stoma seal 14 may be configured to have a non-smooth surface structure and/or texture and/or geometry. Such non-smoothness may, for example, be provided by one or more of the following:

(a) Referring to FIG. 7, the surface of the stoma seal 14 may be provided with narrow miniature pathways or channels 40. The pathways/channels 40 may, for example, be of about 0.05 mm to 5 mm in depth and/or of 0.05 mm to 10 mm in width. The pathways/channels 40 may be tortuous. The pathways/channels 40 may extend generally outwardly from the stoma 12. The pathways/channels 40 may guide flatus away from the stoma 12 while the tortuous nature of the pathways/channels 40 may obstruct the flow of faecal matter.

Figure 8:
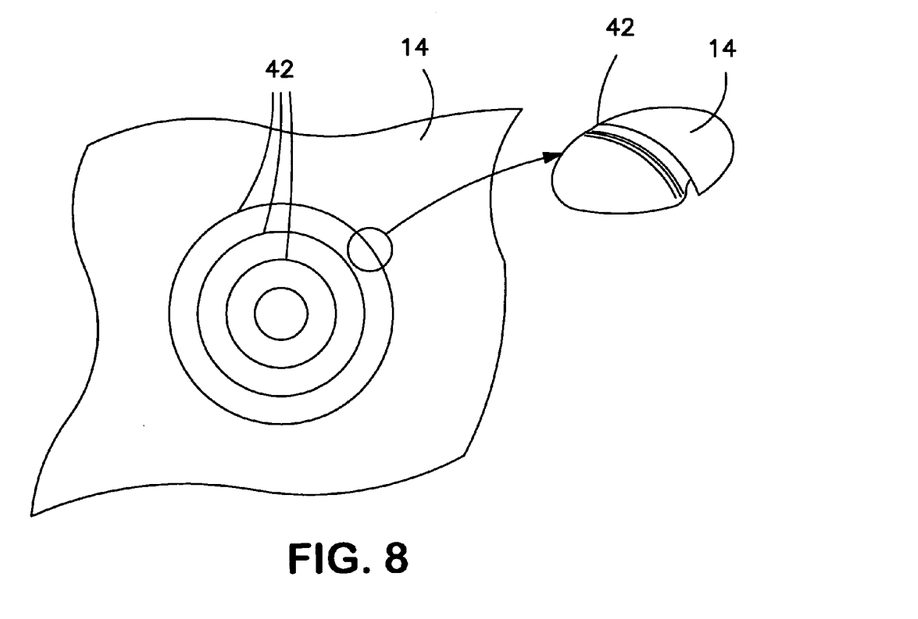
FIG. 8 is a schematic underside perspective view of a further example stoma seal having protruding seals.
Figure 9:
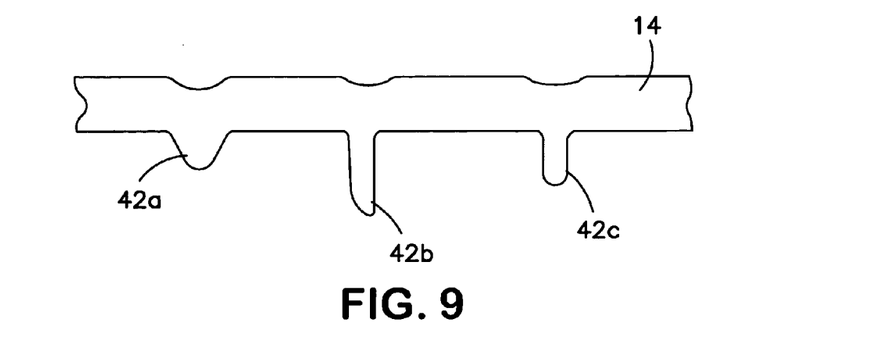
FIG. 9 is a schematic cross-section showing different seal configurations of the stoma seal of FIG. 8.

(b) Referring to FIG. 8, the surface of the stoma seal 14 may be provided with projecting seals 42 for defining successive seals against the stoma 12/peristomal tissue 18. The seals 42 may be configured to present a lateral obstruction or resistance to the passage of faecal matter. The seals 42 may extend generally perpendicularly to the direction in which flatus flows to vent. The seals 42 may have a concentric configuration. Referring to FIG. 9, the seals 42 may have the form of one or more of ridges 42a, flaps 42b and/or ribs 42c.

Figure 10:
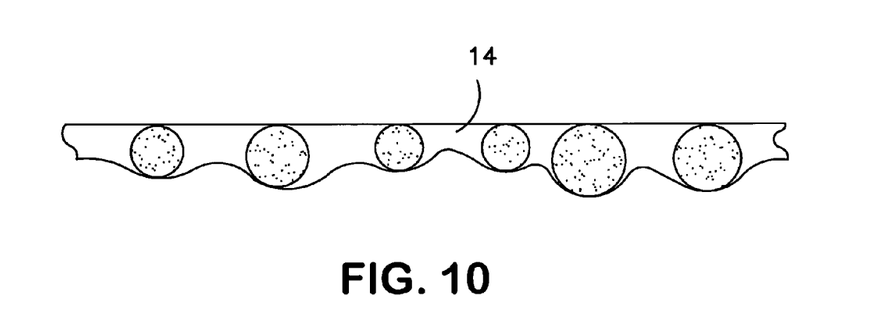
FIG. 10 is a schematic cross-section of a further example stoma seal having a non-smooth contour.

(c) Referring to FIG. 10, the surface of the stoma seal 14 may be contoured so as to be non-flat. The contour may, for example, be at the micro-structure scale. The contour may, for example, be provided by contour defining elements such as fibres or particles, carried on the surface of the stoma seal 14, for example, embedded in a matrix.

Figure 11:
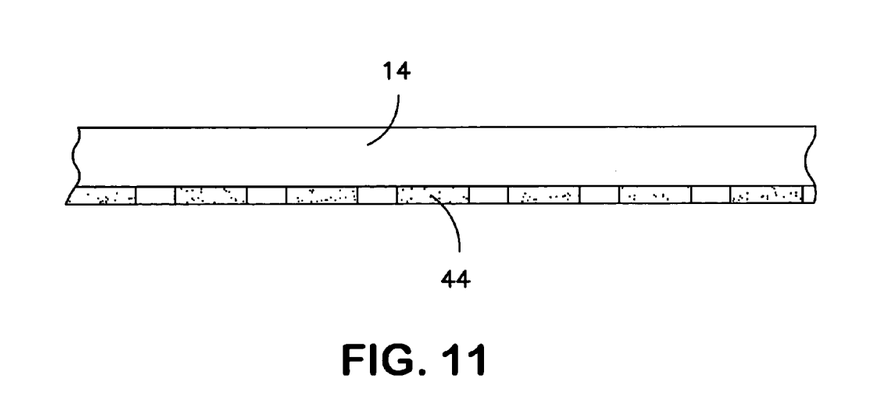
FIG. 11 is a schematic cross-section of a further example stoma seal having an apertured layer.

(d) Referring to FIG. 11, a porous and/or apertured layer 44 may be placed against the stoma seal 14. For example, the layer 44 may be a mesh or net. The layer 44 may be on the surface of the stoma seal 14 facing the stoma 12, or it may surround the stoma seal 14, e.g. be wrapped around the stoma seal 14. The layer 44 may impart a non-smooth surface structure to the stoma seal 14. The scale of the structure may, for example, lie in the range of about 0.01 mm to about 10 mm. In one form, the scale of the structure may lie in the range of from about 0.1 mm to about 0.5 mm.

The non-smoothness illustrated by the foregoing examples may help break up the flow of faecal matter and/or help trapping of liquid and/or solid stool, and/or help flow separation of the gas phase (flatus). In addition, by creating surface induced variations in the cohesive and/or capillary forces in the interface between the surface and the faecal matter, "break-out" paths may be formed along which flatus bubbles may pass through the meniscus at the interface.

Figure 12:
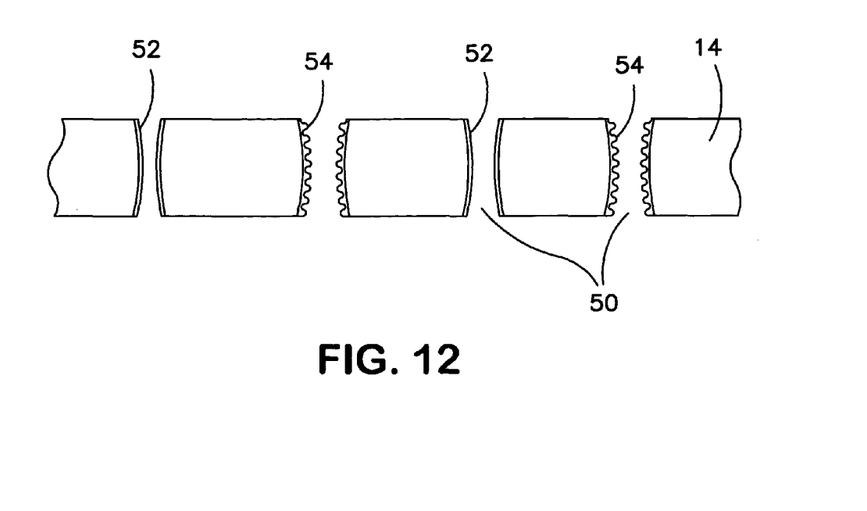
FIG. 12 is a schematic cross-section of a further example porous stoma seal.

In the above, various features may be shown applied to an external surface of the stoma seal 14, for example, the surface facing the stoma 12. However, one or more of the features may be applied to any external or internal surface of the stoma seal 14 that may come into contact with faecal matter. For example, referring to FIG. 12, at least a portion of the stoma seal 14 may be porous, and may comprise apertures 50. The internal surface(s) of the apertures 50 may be provided with one of more of the foregoing features. For example, the internal surface 14 may carry a coating 52 similar to the coating 30 described earlier and/or the internal surface may have non-smooth surface features 54.

Figure 13:
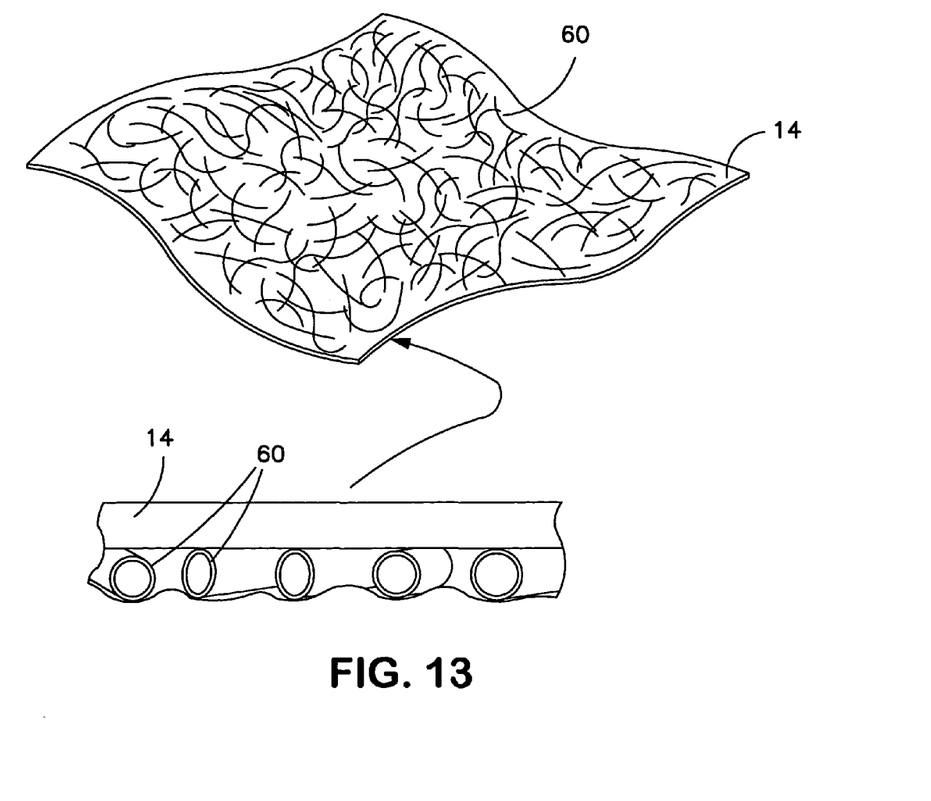
FIG. 13 is schematic view of a further example stoma seal comprising multiple elements.

In an alternative form, the stoma seal 14 may comprise a multiplicity of elements. For example, referring to FIG. 13, the elements may comprise fibres, filaments or tubes 60. The elements may be arranged as a mesh or web, either singly or in bundles. The elements may be woven together or nonwoven. In a similar manner to that that described above, the internal and/or external surface(s) of the elements may be provided with any of the aforementioned properties for aiding separation of the flatus gas at the interface between the faecal matter and the stoma seal 14.

The foregoing description is merely illustrative of preferred forms of the invention. Many modifications, improvements and equivalents may be used within the scope and/or spirit of the invention.

The invention claimed is:

1. A controlled evacuation appliance for an ostomate, comprising:
    a housing attachable to the ostomate around the mouth of a stoma, said housing at least one vent port for venting of flatus;
    a stoma seal in communication with said housing, said stoma seal including a membrane covering the mouth of the stoma when said housing is attached around the stoma, and a resiliently compressible foam support supporting said membrane of said stoma seal, said membrane being pressed by said a resiliently compressible foam support against the mouth of the stoma obstructing the passage of fecal matter excreted from the stoma, wherein said stoma seal allows flatus to pass through said at least one vent in said housing while obstructing the passage of fecal matter when said housing is attached to the ostomate; and
    a cover layer placed against the stoma seal on the surface of the stoma seal facing the stoma, the cover layer having a non-smooth structure on the surface facing the stoma, wherein the non-smooth structure on the cover layer is capable of trapping liquid or solid stool and increasing gas separation to facilitate venting of flatus gas.

2. The controlled evacuation appliance of claim 1, wherein the stoma seal further comprises carbon.

3. The controlled evacuation appliance of claim 1, wherein the stoma seal comprises a microstructure.

4. The controlled evacuation appliance of claim 1, wherein the stoma seal comprises a plurality of channels.

5. The controlled evacuation appliance of claim 4, wherein the channels are tortuous.

6. The controlled evacuation appliance of claim 5, wherein the projecting ridges and/or ribs extend perpendicular to the direction in which flatus flows to vent.

7. The controlled evacuation appliance of claim 4, wherein the channels extend in the direction in which flatus vents away from the stoma.

8. The controlled evacuation appliance of claim 1, wherein at least a portion of the stoma seal has a micro-rough coating.

9. The controlled evacuation appliance of claim 1, wherein the cover layer is porous.

10. The controlled evacuation appliance of claim 1, wherein the cover layer is apertured.

11. The controlled evacuation appliance of claim 1, wherein the stoma seal is porous.

* * * * *